US012629210B2

(12) United States Patent
Miike et al.

(10) Patent No.:  US 12,629,210 B2
(45) Date of Patent:  May 19, 2026

(54) MEDICAL TUBE POSITION CONFIRMATION SYSTEM

(71) Applicants: Otsuka Pharmaceutical Factory, Inc., Tokushima (JP); PAX CO., LTD., Tokyo (JP); OTSUKA CLINICAL SOLUTIONS, INC., Ikinawa-ken (JP)

(72) Inventors: Shinya Miike, Tokyo (JP); Yutaka Suzuki, Tokyo (JP)

(73) Assignees: Otsuka Pharmaceutical Factory, Inc., Tokushima (JP); Pax Co., Ltd., Tokyo (JP); Otsuka Clinical Solutions, Inc., Ikinawa-ken (JP)

( * ) Notice: Subject to any disclaimer, the term of this patent is extended or adjusted under 35 U.S.C. 154(b) by 141 days.

(21) Appl. No.: 16/771,958

(22) PCT Filed: May 7, 2018

(86) PCT No.: PCT/JP2018/017651
§ 371 (c)(1),
(2) Date: Jun. 11, 2020

(87) PCT Pub. No.: WO2019/215791
PCT Pub. Date: Nov. 14, 2019

(65) Prior Publication Data
US 2021/0169580 A1     Jun. 10, 2021

(51) Int. Cl.
A61B 34/20        (2016.01)
A61J 15/00        (2006.01)

(52) U.S. Cl.
CPC ........... A61B 34/20 (2016.02); A61J 15/0003 (2013.01); A61B 2034/2055 (2016.02)

(58) Field of Classification Search
USPC ........................................................ 600/424
See application file for complete search history.

(56) References Cited

U.S. PATENT DOCUMENTS

| | | | |
|---|---|---|---|
| 2006/0036164 A1* | 2/2006 | Wilson | A61B 5/06 600/424 |
| 2017/0065491 A1 | 3/2017 | Waitzman et al. | |

FOREIGN PATENT DOCUMENTS

| | | |
|---|---|---|
| JP | 2008518738 | 6/2008 |
| JP | 2010528818 A | 8/2010 |
| | (Continued) | |

OTHER PUBLICATIONS

PCT International Search Report and Written Opinion mailed Jun. 26, 2018, issued in corresponding International Application No. PCT/JP2018/017651 (10 pgs.).

*Primary Examiner* — Christopher Koharski
*Assistant Examiner* — Renee C Langhals
(74) *Attorney, Agent, or Firm* — Finnegan, Henderson, Farabow, Garrett & Dunner, LLP

(57) ABSTRACT
A medical tube position confirmation system for confirming the position of a medical tube that is used to supply nutrients to the interior of a body by means of tube feeding while an end portion thereof is inserted into (placed in) the stomach includes a light guide that is configured to guide light entering through an incident end portion so that the light exits through an exit end portion, and is configured to be insertable into the medical tube so that the exit end portion is disposed in the interior of the stomach, and a light source that is optically connected to the incident end portion of the light guide and emits light containing wavelengths that pass through a living body.

8 Claims, 5 Drawing Sheets

(56) References Cited

FOREIGN PATENT DOCUMENTS

| JP | 2013198644 A | * | 10/2013 |
| JP | 2015016137 A | | 1/2015 |
| JP | 2015066018 A | | 4/2015 |
| JP | 2016077450 A | | 5/2016 |
| JP | 2016087091 A | | 5/2016 |
| JP | WO2015133119 A1 | | 4/2017 |
| JP | 7069161 B2 | | 5/2022 |
| WO | WO2013-171870 A1 | | 11/2013 |

* cited by examiner

CAMERA

30

IMAGE SENSOR
31

Lout

STORAGE UNIT
33

PROCESSING UNIT
32

COMMUNICATION UNIT
34

MEDICAL TUBE POSITION CONFIRMATION SYSTEM

CROSS-REFERENCE TO RELATED PATENT APPLICATIONS

This application is a national stage filing under 35 U.S.C. § 371 of International Application No. PCT/JP2018/017651, filed May 7, 2018, the contents of which are incorporated herein by reference in its entirety.

TECHNICAL FIELD

The present invention relates to a medical tube position confirmation system.

BACKGROUND ART

Conventionally, in a medical setting, food is supplied directly into the stomach of a patient who finds oral ingestion of food difficult using a method known as nasal tube feeding. More specifically, a soft nasal tube is inserted through the nasal cavity of the patient until a tip end portion thereof reaches the stomach, whereupon liquid food and nutritional supplements are injected through a base end portion of the tube.

During nasal tube feeding, a method of inserting a nasal tube coated with lubricating jelly into the nostril, having the patient perform a swallowing action repeatedly while feeding the tip end portion of the tube more deeply little by little, and guiding the tip end portion of the nasal tube toward the esophagus side until the tip end portion reaches the stomach is implemented.

However, the back of the throat of a human bifurcates into two passages, namely the trachea and the esophagus, making the operation to insert the nasal tube extremely difficult, and when food or the like enters the lungs mistakenly, aspiration pneumonia or the like may occur. It is therefore necessary to perform an operation to confirm that the tip end portion of the nasal tube has reached the stomach.

Patent Document 1 discloses a detection line having a pair of insulated wires and a sensor portion formed on the tip end thereof. The detection line is inserted into a medical tube so that when the sensor portion comes into contact with gastric juice, a resistance value between the pair of insulated wires varies. Hence, by detecting variation in the resistance value between the pair of insulated wires, it can be determined that the sensor portion has come into contact with gastric juice and accordingly that the medical tube has correctly reached the stomach.

Further, Patent Document 2 discloses a nasal tube tip end position confirmation device including a casing, a connecting portion that communicates with the outside from the casing and is connected to a base end side of a nasal tube inserted into the body of a patient, a sensor element disposed in the casing, an electronic circuit, and display means. The electronic circuit outputs air pressure variation received by the sensor element in the form of an electric signal, and the display means receives the output from the electronic circuit and displays the air pressure variation in a recognizable state. Hence, by pressing the abdomen of the patient from the outside, air pressure variation is generated in the stomach, and by having the display means display information indicating that the sensor element has received the air pressure variation, it is possible to determine whether or not the nasal tube has been inserted to an appropriate position.

CITATION LIST

Patent Document

Patent Document 1: Patent Publication JP-A-2016-77450
Patent Document 2: Japanese Patent No. 6245870

SUMMARY

Technical Problem

However, with a method employing a detection line, such as that of Patent Document 1, it is necessary for gastric juice to be secreted in an appropriate location. This means that the types of patients to which the method can be applied are limited, and runs counter to the aim of determining the position of the medical tube with precision. Further, with a method employing air pressure variation, such as that of Patent Document 2, a complicated configuration is required to control the air pressure, leading to an increase in manufacturing cost.

An object of the present invention is therefore to provide a medical tube position confirmation system with which the position of a medical tube can be confirmed more easily.

Solution to Problem

A medical tube position confirmation system according to an aspect of the present invention is a medical tube position confirmation system for confirming the position of a medical tube that is used to supply nutrients to the interior of a body by means of tube feeding while an end portion thereof is inserted into (placed in) the stomach. The system includes a light guide that is configured to guide light entering through an incident end portion so that the light exits through an exit end portion and is inserted into the medical tube so that the exit end portion is disposed in the interior of the stomach, and a light source that is optically connected to the incident end portion of the light guide and emits light containing wavelengths that pass through a living body.

According to this aspect, the light emitted from the light source, which contains wavelengths that pass through a living body, is guided through the interior of the light guide inserted into the medical tube so as to exit through the exit end portion of the light guide, which is disposed in the stomach. Having exited through the exit end portion, the light then passes through the stomach and the living body. Hence, an operator can confirm the position of the medical tube by checking the position in which the light passes through the stomach and the living body from the exterior of the living body.

Advantageous Effects of Invention

According to the present invention, it is possible to provide a medical tube position confirmation system with which the position of a medical tube can be confirmed more easily.

BRIEF DESCRIPTION OF DRAWINGS

FIG. 2 is a schematic view showing an example of a functional configuration of a light 10.

FIG. 4 is a schematic view showing an example of a functional configuration of a camera 30.

DESCRIPTION OF EMBODIMENTS

Figure 1:
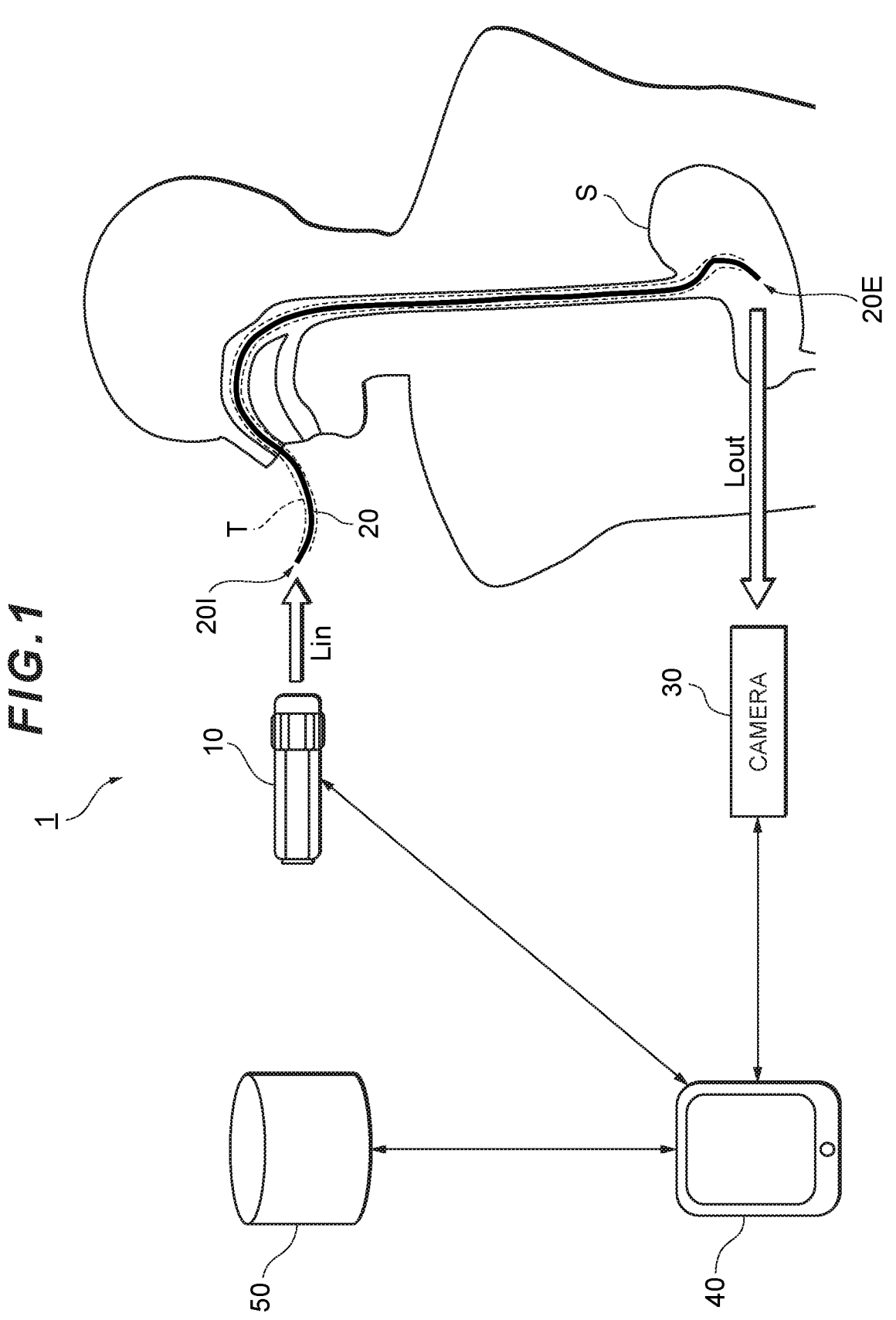
FIG. 1 is a pattern diagram showing an example of a configuration of a medical tube position confirmation system 1 according to an embodiment of the present invention.

Referring to the attached figures, a preferred embodiment of the present invention will be described (note that in the figures, identical reference numerals denote identical or similar configurations).

(1) Overall Configuration

FIG. 1 is a pattern diagram showing an example of a configuration of a medical tube position confirmation system 1 according to an embodiment of the present invention. As shown in FIG. 1, the medical tube position confirmation system 1 includes, for example, a light 10, an optical fiber 20, a camera 30, a user terminal 40, and a database 50. The user terminal 40 is connected communicably to each of the light 10, the camera 30, and the database 50 via a communication network.

(2) Configurations of Respective Parts (2-1) Light 10

Figure 2:
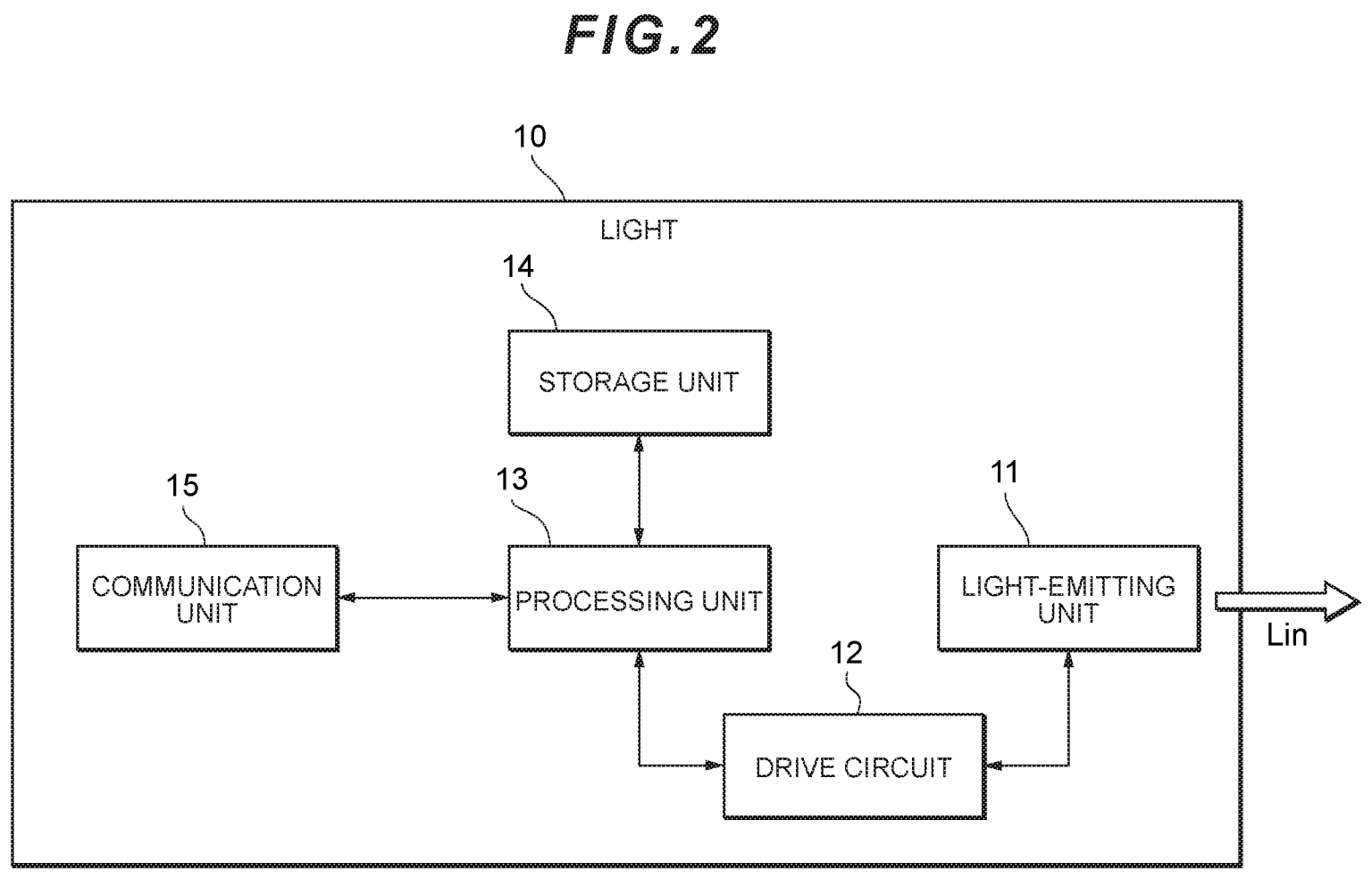

FIG. 2 is a schematic view showing an example of a functional configuration of the light 10. The light 10 is an example of a light source that emits light containing wavelengths that pass through a living body. The light 10 is formed by providing a light-emitting unit 11, a drive circuit 12, a processing unit 13, a storage unit 14, and a communication unit 15 in a substantially cylindrical casing formed from metal, resin, or the like, for example.

The light-emitting unit 11 is constituted by a light-emitting LED, for example, and emits light containing wavelengths that pass through a living body. When the light 10 receives a supply of electric energy from a power supply (not shown) via the drive circuit 12 while a switch (not shown) provided on the light 10 is switched ON, the light 10 emits light of predetermined wavelengths by converting the electric energy into optical energy. Note that the light-emitting unit 11 is not limited to a light-emitting LED and may be any light-emitting body that emits light containing a wavelength that passes through a living body.

The light 10 is optically connected to an incident end portion 20I of the optical fiber 20, to be described below, so that the light emitted by the light-emitting unit 11 of the light 10 enters the incident end portion 20I of the optical fiber 20.

The processing unit 13 is a CPU or the like, for example, having one or a plurality of processors and corresponding peripheral circuits, and performs overall control of the entire operation of the light 10 on the basis of a program or the like stored in the storage unit 14.

The storage unit 14 is constituted by a nonvolatile memory or the like, such as an EEPROM (Electronically Erasable and Programmable Read Only Memory), for example, and stores preset control information and the like relating to the light 10.

The communication unit 15 includes a communication interface circuit for connecting the light 10 to the communication network, and communicates with the communication network. Note that the light 10 may have a simpler configuration not including the communication unit 15 and so on.

Figure 3:
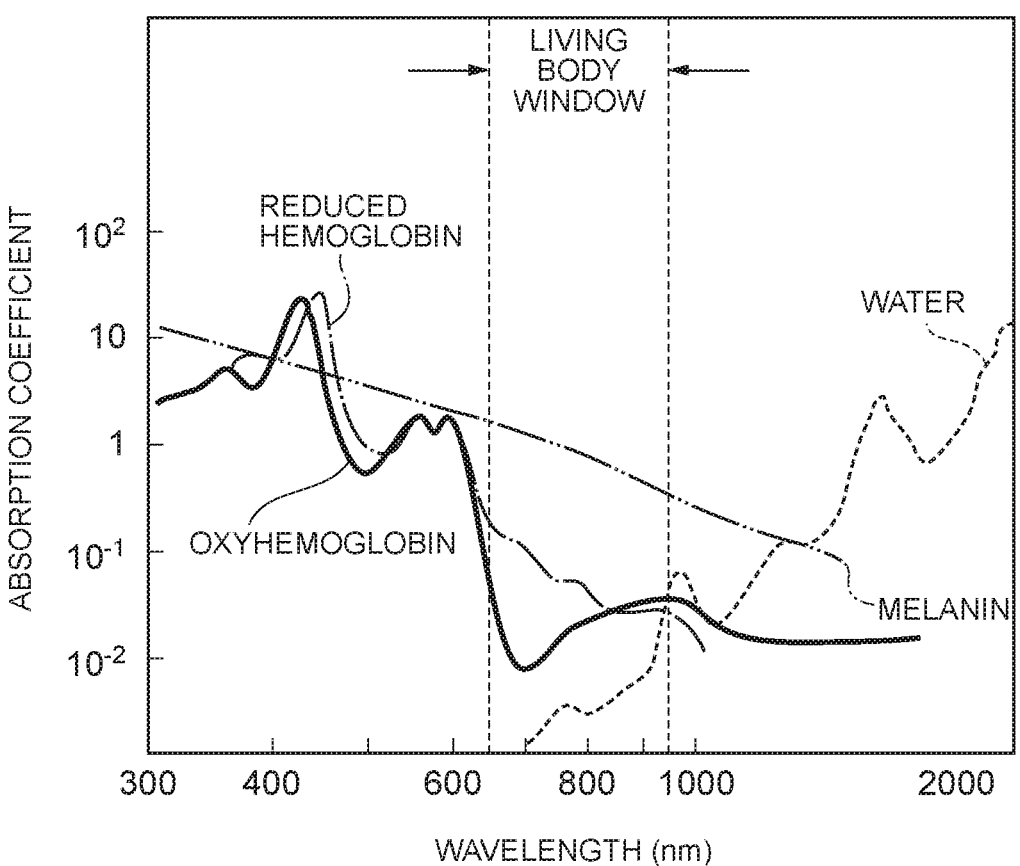
FIG. 3 is a view illustrating wavelengths of light emitted by the light 10.

Here, using FIG. 3, the wavelengths of the light emitted by the light 10 will be described. FIG. 3 shows the light absorption coefficient of each of oxyhemoglobin, reduced hemoglobin, melanin, and water, which are the main constituent elements of a living body. On the graph in FIG. 3, the horizontal axis shows the wavelength (nm) and the vertical axis shows the absorption coefficient.

As shown in FIG. 3, absorption by blood (in other words, hemoglobin) is high in a wavelength region at or below approximately 650 nm, while absorption by water is high in a wavelength region exceeding approximately 950 nm. In a wavelength region of no less than approximately 650 nm and no more than approximately 950 nm, meanwhile, the respective absorption coefficients of hemoglobin and water are comparatively low. It can therefore be said that light in this wavelength region (no less than approximately 650 nm and no more than approximately 950 nm) passes through a living body more easily than light in another wavelength region.

There are no particular limitations on the wavelengths of the light emitted by the light-emitting unit 11 of the light 10 as long as wavelengths that pass through a living body are included therein, but as noted above, the wavelengths preferably include wavelengths within a range of no less than approximately 650 nm and no more than approximately 950 nm.

Further, as shown in FIG. 3, the absorption rate of oxyhemoglobin is particularly low in a wavelength region of no less than approximately 650 nm and no more than approximately 800 nm. Therefore, the wavelengths of the light emitted by the light-emitting unit 11 of the light 10 preferably include at least a part of a wavelength region of no less than approximately 650 nm and no more than approximately 800 nm.

Furthermore, as shown in FIG. 3, the absorption rate of reduced hemoglobin is particularly low in a wavelength range of no less than approximately 800 nm and no more than approximately 950 nm. Therefore, the wavelengths of the light emitted by the light-emitting unit 11 of the light 10 preferably include at least a part of a wavelength region of no less than approximately 800 nm and no more than approximately 950 nm.

Moreover, as shown in FIG. 3, the absorption rate of water is particularly low in a wavelength range of no less than approximately 650 nm and no more than approximately 700 nm. Therefore, the wavelengths of the light emitted by the light-emitting unit 11 of the light 10 preferably include at least a part of a wavelength region of no less than approximately 650 nm and no more than approximately 700 nm.

(2-2) Optical Fiber 20

The optical fiber 20 is an example of a light guide that takes the shape of a narrow, flexible fiber, for example, and can be inserted into the interior of a medical tube T, as shown in FIG. 1. The optical fiber 20 has a two-layer structure constituted by, for example, a central core (not shown) formed from silica glass, plastic, or the like, and cladding (not shown) covering the periphery of the central core.

As shown in FIG. 1, the incident end portion 20I through which the light emitted by the light 10 and so on enters is formed on one end of the optical fiber 20. The incident end portion 20I is positioned so as to be optically connectable to the light 10 in a state where the optical fiber 20 is inserted into the interior of the medical tube T.

Further, as shown in FIG. 1, an exit end portion 20E through which the light exits is formed on the other end of the optical fiber 20. When the optical fiber 20 correctly reaches the stomach while inserted into the interior of the medical tube T, the exit end portion 20E is disposed inside the stomach (indicated by a reference symbol S in FIG. 1).

The refractive index of the core of the optical fiber 20 is set to be higher than the refractive index of the cladding of the optical fiber 20. Accordingly, the light entering through the incident end portion 20I is totally reflected on the boundary between the core and the cladding so as to propagate through the core. Having propagated through the core and reached the exit end portion 20E, the light exits through the exit end portion 20E. Having exited through the exit end portion 20E, the light passes through the stomach and other body parts and exits the living body so as to partially reach the camera 30.

(2-3) Camera 30

Figure 4:
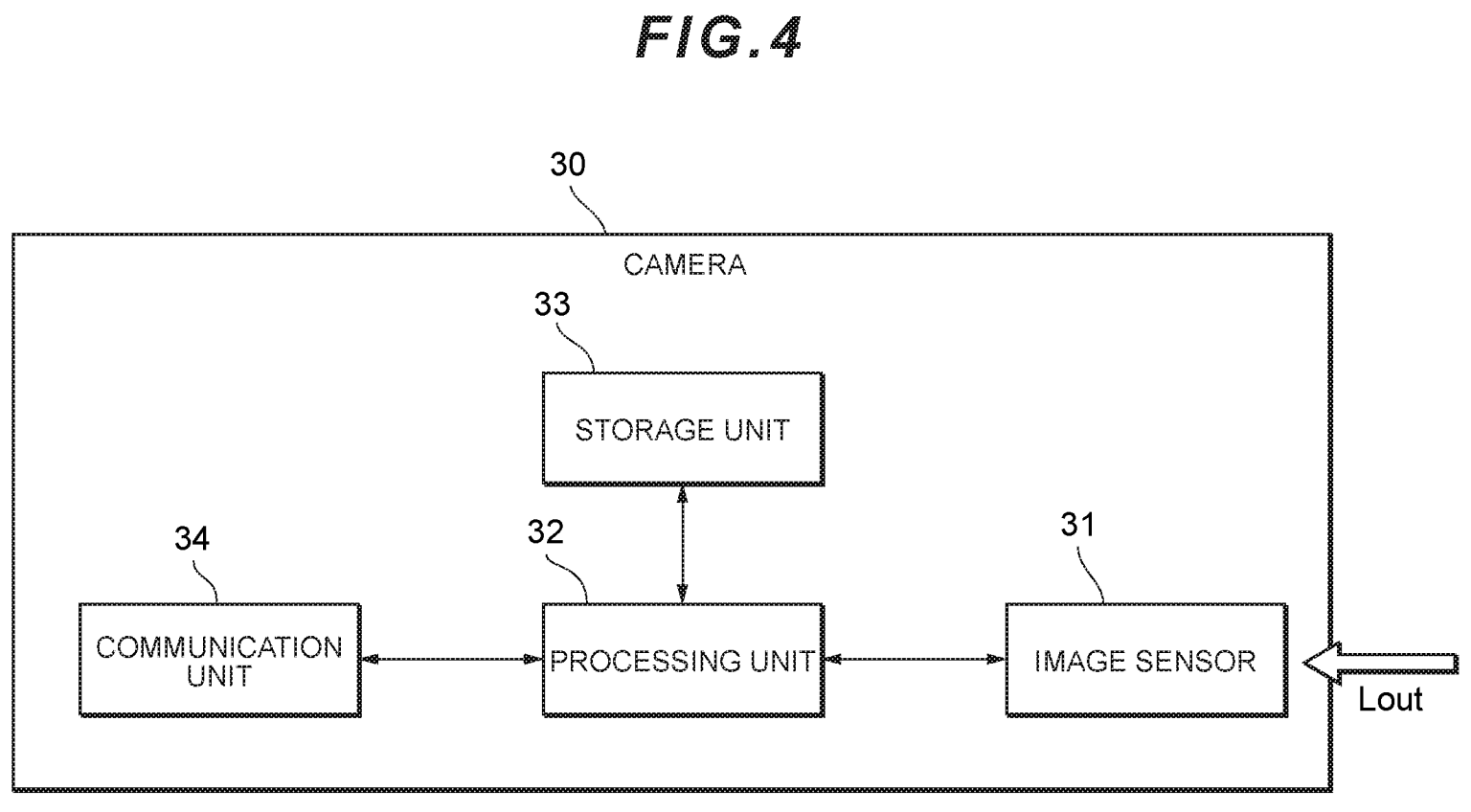

FIG. 4 is a schematic view showing an example of a functional configuration of the camera 30.

The camera 30 is an example of an imaging unit that generates image data by capturing an image of the living body (including a part of the living body) on the basis of at least the light that passes through the living body after exiting through the exit end portion 20E of the optical fiber 20. The camera 30 includes, for example, an image sensor 31, a processing unit 32, a storage unit 33, and a communication unit 34. The camera 30 may be a camera that is particularly sensitive to infrared rays, for example.

The image sensor 31 is constituted by a CCD (a Charge Coupled Device), a CMOS (a Complementary Metal Oxide Semiconductor), or the like, for example, and under the control of the processing unit 32, the image sensor 31 detects light that has been condensed by a lens, not shown in the figure, and converts the light into an electric signal.

The processing unit 32 is a CPU or the like, for example, having one or a plurality of processors and corresponding peripheral circuits, and performs overall control of the entire operation of the information processing device on the basis of a program or the like stored in the storage unit 33. The processing unit 32 generates image data on the basis of the electric signal generated by the image sensor 31, for example. Further, the processing unit 32 transmits the generated image data to the user terminal 40 or the database 50 via the communication unit 34.

The storage unit 33 includes at least one of a magnetic tape device, a magnetic disk device, and an optical disk device, for example, and stores a computer program, data, and so on used in the processing executed by the processing unit. The storage unit 33 is an example of an image data storage unit for storing the image data generated when the camera 30 captures an image of the living body.

The communication unit 34 includes a communication interface circuit for connecting the camera 30 to the communication network, and communicates with the communication network.

Note that the camera 30 may also include a display unit (not shown) for displaying the image data generated by the processing unit 32 and so on.

(2-4) User Terminal 40

Figure 5:
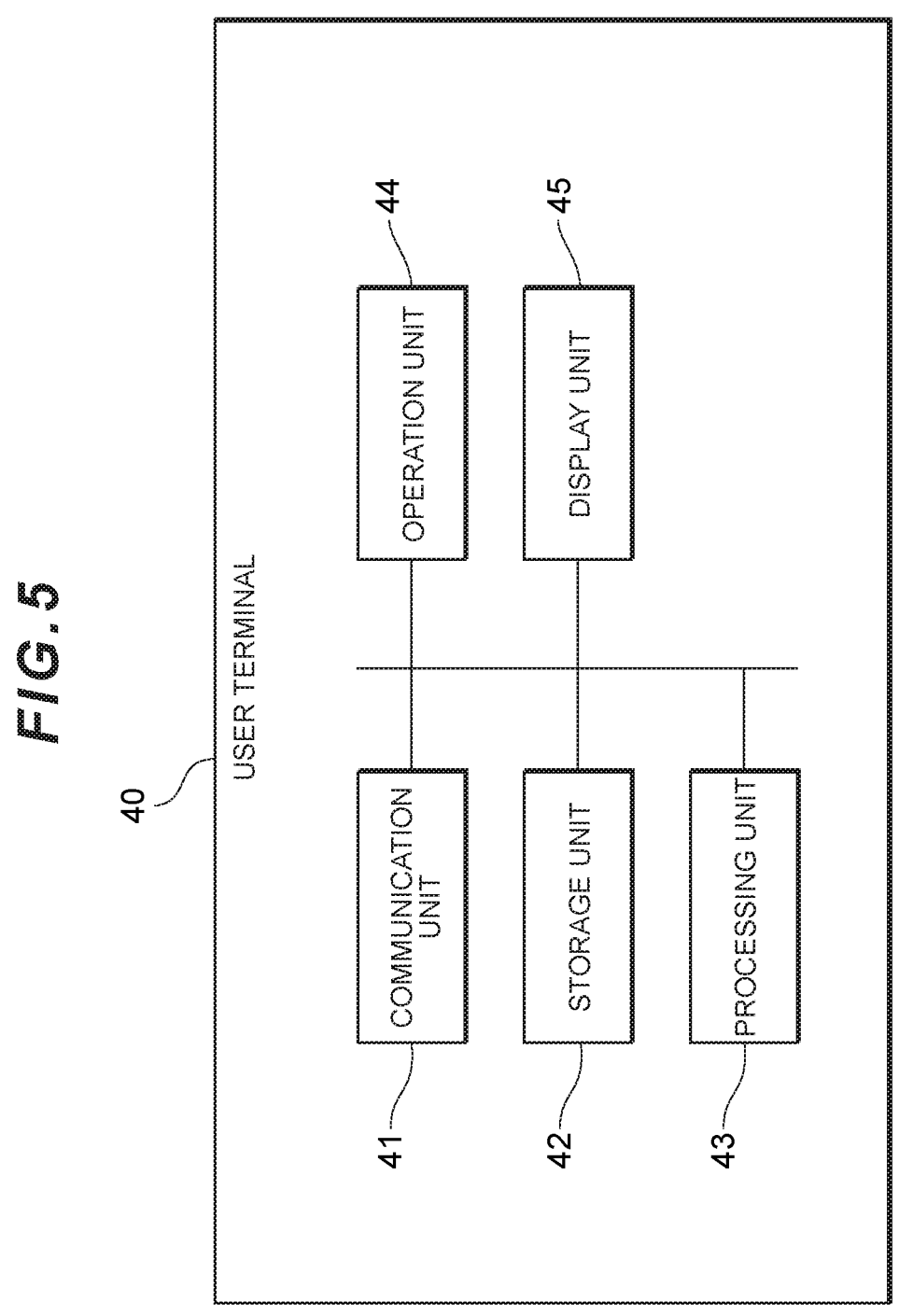
FIG. 5 is a schematic view showing an example of a functional configuration of a user terminal 40.

FIG. 5 is a schematic view showing an example of a functional configuration of the user terminal 40. The user terminal 40 may be any general-purpose information processing terminal and includes, for example, a communication unit 41, a storage unit 42, a processing unit 43, an operation unit 44, a display unit 45, and so on.

The communication unit 41 includes a communication interface circuit for connecting the user terminal 40 to the communication network, and communicates with the communication network.

The storage unit 42 includes at least one of a magnetic tape device, a magnetic disk device, and an optical disk device, for example, and stores a computer program, data, and so on used in the processing executed by the processing unit. The storage unit 42 is an example of the image data storage unit for storing the image data generated when the camera 30 captures an image of the living body.

The processing unit 43 is a CPU or the like, for example, having one or a plurality of processors and corresponding peripheral circuits, and performs overall control of the entire operation of the information processing device on the basis of a program or the like stored in the storage unit. The processing unit 43 may determine whether or not the position of the medical tube T is appropriate by analyzing image data received from the camera 30 over the communication network. Further, the processing unit 13 may transmit the image data received from the camera 30 over the communication network to the database 50, for example. Furthermore, the processing unit 13 may transmit a control signal for switching the switch of the light 10 ON and OFF to the light 10, for example.

The operation unit 44 is constituted by a touch panel, key buttons, or the like, for example, and serves to receive operations performed by a user to input alphabetic characters, numerals, symbols, and so on and supply signals corresponding to the operations to the processing unit.

The display unit 45 is constituted by a liquid crystal display, an organic EL (Electro-Luminescence) display, or the like, for example, and displays images based on display data supplied from the processing unit and so on.

(2-5) Database 50

The database 50 is a database managed by a medical institution such as a hospital, for example, and includes at least one of a magnetic tape device, a magnetic disk device, and an optical disk device. The database 50 receives image data from the camera 30 or the user terminal 40, for example, and stores the received image data. In other words, the database 50 is an example of the image data storage unit for storing the image data generated when the camera 30 captures an image of the living body. The database 50 may be connected to an external information processing device, such as a management server used by a medical institution or the like, for example, via a communication network. The external information processing device may obtain the image data stored in the database 50 and execute processing corresponding to various aims on the image data.

(3) Use Method and Operation

Next, a use method and an operation of the medical tube position confirmation system 1 will be described.

First, an operator checks the end portion of the medical tube T in the nasal cavity or the like of the patient and then inserts the optical fiber 20 into the interior of the medical tube T by a predetermined length, starting with the exit end portion 20E.

Next, the switch (not shown) provided on the light 10 is switched ON so that the light 10 emits light. At this time, the operator may cause the light 10 to emit light by operating the switch of the light 10, for example. Alternatively, the operator may cause the light 10 to emit light by operating the user terminal 40 so that a control signal for switching the switch of the light 10 ON is transmitted from the user terminal 40 to the light 10.

When the light 10 emits light, the light emitted by the light 10 enters the incident end portion 20I of the optical fiber 20. The light that enters the incident end portion 20I propagates through the interior of the optical fiber 20 by total reflection so as to reach the exit end portion 20E. Having reached the exit end portion 20E, the light exits through the exit end portion 20E and passes through the body of the patient.

The operator then checks the position of the light passing through the body of the patient in order to determine whether or not the position of the light is a position corresponding to the stomach. When the position of the light is a position corresponding to the stomach, it can be determined that the medical tube T has reaches the stomach appropriately. When the position of the light is not a position corresponding to the stomach or when the presence of the light cannot be confirmed, it can be determined that the medical tube T has not reached the stomach. Here, the position of the light may be checked using either a method of visual confirmation by the operator or a method employing the image data generated by the camera 30. In the method employing the image data generated by the camera 30, for example, the user terminal 40 receives from the camera 30 the image data generated by the camera 30 on the basis of at least the light passing through the stomach and other body parts. The user terminal 40 then analyzes the image data to determine whether or not the position of the light is a position corresponding to the stomach.

(4) Miscellaneous

Note that generally, the optical intensity required for light to pass from the interior of the stomach to the exterior of the body is lower than the optical intensity required for light to pass from the interior of the lungs and trachea to the exterior of the body. Therefore, the light source, such as the light 10, may be set to emit light at an intensity that equals or exceeds a first intensity required for light to pass from the interior of the stomach to the exterior of the body but is lower than a second intensity required for light to pass from the interior of the lungs and trachea to the exterior of the body. According to this configuration, there is no need to determine the position of the stomach during visual confirmation of the light by the operator or analysis of the image data, and it can be determined that the medical tube T has appropriately reached the stomach simply by determining whether or not the light can be confirmed.

The embodiment described above is to be used to facilitate understanding of the present invention, and the present invention is not limited thereto. The elements included in the embodiment, as well as the arrangements, materials, conditions, shapes, sizes, and so on thereof, are not limited to the cited examples and may be modified as appropriate. Moreover, configurations illustrated in different embodiments may be partially replaced or combined.

REFERENCE SIGNS LIST

1 Medical tube position confirmation system
10 Light
11 Light-emitting unit
12 Drive circuit
13 Processing unit
14 Storage unit
15 Communication unit
20 Optical fiber
20I Incident end portion
20E Exit end portion
30 Camera
31 Image sensor
32 Processing unit
33 Storage unit
34 Communication unit
40 User terminal
41 Communication unit
42 Storage unit
43 Processing unit 44 Operation unit
45 Display unit

What is claimed is:

1. A medical tube position confirmation system for confirming the position of a medical tube that is used to supply nutrients to an interior of a body by means of tube feeding while an end portion thereof is inserted into (placed in) the stomach, the system comprising:
a light guide that is configured to guide light entering through an incident end portion so that the light exits through an exit end portion, and is configured to be insertable into the medical tube so that the exit end portion is disposed in the interior of the stomach; and
a light source that is optically connected to the incident end portion of the light guide and emits light containing wavelengths in a region of 650 nm or more and 950 nm or less that pass through a living body,
wherein the light source is set to emit light at an intensity that equals or exceeds a first intensity required for light to pass from the interior of the stomach to the exterior of the body but is lower than a second intensity required for light to pass from the interior of the lungs and trachea to the exterior of the body.

2. The medical tube position confirmation system according to claim 1, further comprising an imaging unit for capturing an image of the living body on the basis of at least the light that exits through the exit end portion of the light guide and passes through the living body.

3. The medical tube position confirmation system according to claim 2, further comprising an image data storage unit for storing image data generated when the imaging unit captures an image of the living body.

4. The medical tube position confirmation system according to claim 1, further comprising a processing unit configured to control the light source to emit light at an intensity that equals or exceeds the first intensity but is lower than the second intensity.

5. The medical tube position confirmation system according to claim 4, further comprising a storage unit for storing control information, wherein the processing unit is configured to control the light source to emit light at an intensity that equals or exceeds the first intensity but is lower than the second intensity based on the control information stored in the storage unit.

6. A method of confirming the position of a medical tube that is used to supply nutrients to an interior of a body by means of tube feeding while an end portion thereof is inserted into (placed in) the stomach, which comprises the steps of:
inserting a light guide configured to guide light entering through an incident end portion so that the light exits through an exit end portion into the medical tube by a predetermined length, starting with the exit end portion;
optically connecting a light source that emits light containing wavelengths in a region of 650 nm or more and 950 nm or less that pass through a living body to the incident end portion of the light guide; and
causing the light source to emit light
wherein the light source is set to emit light at an intensity that equals or exceeds a first intensity required for light to pass from the interior of the stomach to the exterior of the body but is lower than a second intensity required for light to pass from the interior of the lungs and trachea to the exterior of the body.

7. The method according to claim 6, further comprising the step of controlling the light source to emit light at an intensity that equals or exceeds the first intensity but is lower than the second intensity.

8. The method according to claim 7, wherein the step of controlling the light source to emit light at an intensity that equals or exceeds the first intensity but is lower than the second intensity is performed based on control information.

\* \* \* \* \*